(12) United States Patent
Anderson et al.

(10) Patent No.: US 8,697,900 B2
(45) Date of Patent: *Apr. 15, 2014

(54) METHOD OF PREPARING A DIORGANODIHALOSILANE

(75) Inventors: Kurt Anderson, Crestwood, KY (US);
Aswini Dash, Midland, MI (US);
Charles Hall, Crestwood, KY (US);
Dimitris Katsoulis, Midland, MI (US);
Jonathan Wineland, Bedford, KY (US)

(73) Assignee: Dow Corning Corporation, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/988,178

(22) PCT Filed: Jan. 20, 2012

(86) PCT No.: PCT/US2012/022001
§ 371 (c)(1),
(2), (4) Date: May 17, 2013

(87) PCT Pub. No.: WO2012/102957
PCT Pub. Date: Aug. 2, 2012

(65) Prior Publication Data
US 2013/0310534 A1    Nov. 21, 2013

Related U.S. Application Data

(60) Provisional application No. 61/435,829, filed on Jan. 25, 2011.

(51) Int. Cl.
*C07F 7/00* (2006.01)

(52) U.S. Cl.
USPC ........................................................ 556/466

(58) Field of Classification Search
USPC ........................................................ 556/466
See application file for complete search history.

(56) References Cited

U.S. PATENT DOCUMENTS

| 2,403,370 | A | 7/1946 | Hurd |
| 2,888,476 | A | 5/1959 | Little et al. |
| 3,057,686 | A | 10/1962 | Muetterties |
| 4,314,908 | A | 2/1982 | Downing et al. |
| 4,526,769 | A | 7/1985 | Ingle et al. |
| 4,836,997 | A | 6/1989 | Lepage et al. |
| 4,888,435 | A | 12/1989 | Chadwick et al. |
| 4,946,980 | A | 8/1990 | Halm et al. |
| 4,973,725 | A | 11/1990 | Lewis et al. |
| 6,156,380 | A | 12/2000 | Aramata et al. |
| 6,790,749 | B2 | 9/2004 | Takemura et al. |
| 6,887,448 | B2 | 5/2005 | Block |
| 7,212,778 | B2 | 5/2007 | Hisakuni |
| 7,223,879 | B2 | 5/2007 | Buchwald et al. |
| 7,442,824 | B2 | 10/2008 | Paetzold et al. |
| 7,716,590 | B1 | 5/2010 | Nathan |
| 7,728,176 | B2 | 6/2010 | Masaoka |
| 2005/0074387 | A1 | 4/2005 | Bulan et al. |
| 2010/0280295 | A1 | 11/2010 | Armbruester |

FOREIGN PATENT DOCUMENTS

| DE | 3024319 | 1/1982 |
| DE | 19654154 | 6/1997 |
| EP | 0028009 A2 | 5/1981 |
| EP | 0348902 A2 | 1/1990 |
| EP | 348902 A2 * | 1/1990 |
| JP | 51-23226 | 2/1976 |
| JP | 2009111202 | 5/2009 |
| WO | 2012-123159 | 9/2012 |

OTHER PUBLICATIONS

Dallas T. Hurd, The Vapor Phase Alkylation and Hydrogenation of Chlorosilanes, J. Am. Chem. Soc., 1945, 67 (9), pp. 1545-1548.
Eaborn, C. et al., Further studies on reactions of organic halides with disilanes catalysed by transition metal complexes, Journal of Organometallic Chemistry, vol. 225, 1982, pp. 331-341.
Golubtsov, S.A. et al., Role of the Products of Partial Chlorination of Silicon in the Formation of Methyltrichlorosilane, Russian Chemical Bulletin, vol. 21, No. 3 (1972), pp. 584-586.
H. Walter, Mechanism of the silicide-catalysed hydrodehalogenation of silicon tetrachloride to trichlorosilane, J. Chem. Soc., Faraday Trans., 1996,92, 4605-4608.
Juszczyk et al., of Pd/SiO2 catalysts during high temperature reduction., Department of Catalysis on Metals, Institute of Physical Chemistry, Polish Academy of Sciences, Warsaw, Pol. Catalysis Letters (2002), 78(1-4), 95-98.
Juszczyk et al., Transformation of Pd/SiO2 into palladium silicide during reduction at 450° and 500° C., Institute of Physical Chemistry, Department of Catalysis on Metals, Polish Academy of Sciences, Warsaw, Pol. Journal of Catalysis (2003), 220(2), 299-308.
Lobusevich, N.P. et al., Reactions During Direct Synthesis of Alkylchlorosilanes., vol. 48, No. 11, 1978, pp. 2534-2541.
Moreno-Manas, Marcial et al., Formation of Carbon-Carbon Bonds under Catalysis by Transition-Metal Nanoparticles, Department of Chemistry, Universitat Autonoma de Barcelona, Barcelona, Spain. Accounts of Chemical Research (2003), 36(8), 638-643.
Beccalli, Egle M., et al., C—C, C—O, C—N Bond Formation on sp2 Carbon by Palladium(II)—Catalyzed Reactions Involving Oxidant Agents., Istituto di Chimica Organica A. Marchesini, Facolta di Farmacia, Universita di Milano, Milan, Italy. Chemical Reviews (Washington, DC, United States) (2007), 107(11), 5318-5365.
Methivier, et al., Pd/SiC catalysts. Characterization and catalytic activity for the methane total oxidation.. Institut de Recherches sur la Catalyse—CNRS, conventionne a l'Universite Claude Bernard Lyon 1, Villeurbanne, Fr. Journal of Catalysis (1998), 173(2), 374-382.
Srebowata, A. et al., Hydrodechlorination of 1,2-dichloroethane over differently reduced Pd/SiO2 catalysts., Institute of Physical Chemistry, Polish Academy of Sciences, Warsaw, Pol. Polish Journal of Chemistry (2003), 77(12), 1841-1848.

(Continued)

*Primary Examiner* — Fereydoun G Sajjadi
*Assistant Examiner* — Kofi Adzamli
(74) *Attorney, Agent, or Firm* — Catherine U. Brown

(57) ABSTRACT

A method of preparing a diorganodihalosilane, the method comprising the following separate and consecutive steps: (i) treating a preformed metal silicide with a mixture comprising hydrogen gas and a silicon tetrahalide at a temperature from 300 to 1400° C. to form a treated metal silicide, wherein the preformed metal silicide comprises a metal selected from at least one of Ni, Pd, or Pt; and (ii) reacting the treated metal silicide with an organohalide according to the formula RX at a temperature from 250 to 700° C. to form a diorganodihalosilane, wherein R is $C_1$-$C_{10}$ hydrocarbyl and X is halo.

18 Claims, No Drawings

(56) References Cited

OTHER PUBLICATIONS

Tanaka, Miyoko et al., Nanomaterials Laboratory, National Institute for Materials Science, Tsukuba, Sakura, Japan. Journal of Crystal Growth (2002), 237-239(Pt. 1), 254-258.

Terao, Jun et al., Transition metal-catalyzed C—C bond formation reactions using alkyl halides., Department of Applied Chemistry and Center for Atomic and Molecular Technologies, Graduate School of Engineering, Osaka University, 2-1 Yamadaoka, Suita, Osaka, Japan. Bulletin of the Chemical Society of Japan (2006), 79(5), 663-672.

Vijh, A. K. et al., Discovery of some new stable electrocatalytic materials for the anodic oxidation of hydrazine., Inst. Rech. Hydro-Quebec, Varennes, QC, Can. Journal of Materials Science Letters (1993), 12(2), 113-15.

Vijh, A. K. et al., Electrochemical activity of silicides of some transition metals for the hydrogen evolution reaction in acidic solutions., International Journal of Hydrogen Energy (1990), 15(11), 789-94.

Yin, Lunxiang, et al., Carbon-carbon coupling reactions catalyzed by heterogeneous palladium catalysts., Institute fuer Chemie, Humboldt-Universitaet Berlin, Berlin, Germany. Chemical Reviews (Washington, DC, United States) (2007), 107(1), 133-173.

* cited by examiner

METHOD OF PREPARING A DIORGANODIHALOSILANE

CROSS-REFERENCE TO RELATED APPLICATIONS

This application is a U.S. national stage filing under 35 U.S.C. §371 of PCT Application No. PCT/US12/22001 filed on 20 Jan. 2012, currently pending, which claims the benefit of U.S. Provisional Patent Application No. 61/435,829 filed 25 Jan. 2011 under 35 U.S.C. §119 (e). PCT Application No. PCT/US12/22001 and U.S. Provisional Patent Application No. 61/435,829 are hereby incorporated by reference.

FIELD OF THE INVENTION

The present invention relates to a method of preparing a diorganodihalosilane comprising treating a preformed metal silicide with a mixture comprising hydrogen gas and a silicon tetrahalide to form a treated metal silicide and then reacting the treated metal silicide with an organohalide.

BACKGROUND OF THE INVENTION

Diorganodihalosilanes are hydrolyzed to produce a wide range of polyorganosiloxanes, which are sold into many different industries. Typically, diorganodihalosilanes are produced commercially by the Mueller-Rochow Direct Process, which comprises passing an organohalide, such as methyl chloride, over zero-valent silicon in the presence of a copper catalyst and various promoters. The Direct Process produces a mixture of organohalosilanes, the most valuable of which is dimethyldichlorosilane.

The zero-valent silicon used in the Direct Process is typically made by the carbothermic reduction of $SiO_2$ in an electric arc furnace at extremely high temperatures. Generation of these extreme temperatures requires significant amounts of energy, which adds significant cost to the process of producing zero-valent silicon. Consequently, the use of zero-valent silicon also adds significant costs to the production of diorganodihalosilanes by the Direct Process.

Metal silicides, such as copper silicide, have been used in the direct process to promote the reaction of zero-valent silicon with organohalides to make diorganodihalosilanes. However, when used as a promoter, metal silicides are typically used at low levels with large amounts of zero-valent silicon and other catalysts and promoters.

Therefore, there is a need for more economical processes for producing diorganodihalosilanes that do not directly use zero-valent silicon produced by the carbotherminc reduction of $SiO_2$.

BRIEF SUMMARY OF THE INVENTION

The present invention is directed to a method of preparing a diorganodihalosilane, comprising the following separate and consecutive steps: (i) treating a preformed metal silicide with a mixture comprising hydrogen gas and a silicon tetrahalide at a temperature from 300 to 1400° C. to form a treated metal silicide, wherein the preformed metal silicide comprises a metal selected from at least one of Ni, Pd, or Pt; and (ii) reacting the treated metal silicide with an organohalide according to the formula RX at a temperature from 250 to 700° C. to form a diorganodihalosilane, wherein R is $C_1$-$C_{10}$ hydrocarbyl and X is halo.

Since the method of the invention produces diorganodihalosilanes from silicon tetrahalide and a metal silicide, the method may be more economical than current commercial methods for producing a diorganodihalosilane that directly use zero-valent silicon produced by the carbothermic reduction of $SiO_2$. Further, the method allows for the production of diorganodihalosilanes from metal silicides that normally do not produce diorganodihalosilanes when reacted with an organohalide.

The diorganodihalosilanes produced according to the method of the present invention may be hydrolyzed in known processes to produce polysiloxanes, which find use in many industries and applications.

DETAILED DESCRIPTION OF THE INVENTION

A method of preparing a diorganodihalosilane, the method comprising the following separate and consecutive steps:

(i) treating a preformed metal silicide with a mixture comprising hydrogen gas and a silicon tetrahalide at a temperature from 300 to 1400° C. to form a treated metal silicide, wherein the preformed metal silicide comprises a metal selected from at least one of Ni, Pd, or Pt; and (ii) reacting the treated metal silicide with an organohalide according to the formula RX at a temperature from 250 to 700° C. to form a diorganodihalosilane, wherein R is $C_1$-$C_{10}$ hydrocarbyl and X is halo.

In step (i), a preformed metal silicide is treated with a mixture comprising hydrogen gas and a silicon tetrahalide at a temperature from 300 to 1400° C. to form a treated metal silicide, wherein the preformed metal silicide comprises a metal selected from at least one of Ni, Pd, or Pt.

The preformed metal silicide comprises a metal selected from at least one of Ni, Pd, or Pt, alternatively a metal selected from at least one of Ni or Pd, alternatively Pd. As used herein, "preformed" means that at least a portion of the metal silicide is formed prior to step (i).

The preformed metal silicide may be in a variety of forms, shapes and sizes, up to several centimeters in diameter, but the preformed metal silicide is typically finely-divided. As used herein, "finely divided" means that the preformed metal silicide is in the form of a powder.

Examples of preformed metal silicides include, but are not limited to PdSi, $Pd_2Si$, $Pd_3Si$, $Pd_5Si$, $Pd_2Si_9$, NiSi, $Ni_2Si$, $Ni_3Si$, $NiSi_2$, $Ni_3Si_2$, $Ni_3Si_2$, PtSi, and $Pt_2Si$. In one embodiment, the preformed metal silicide is at least one of PdSi or $Pd_2Si$. The preformed metal silicide may be a mixture of metal silicides.

The preformed metal silicide may be made by methods known in the art. For example, the preformed metal silicide may be made by mixing molten silicon and molten metal in the desired stoichiometric ratios and then cooling to temperatures known in the art to crystallize the desired preformed metal silicide. Once cooled and crystallized, the preformed metal silicide may be subjected to common methods for producing particulate metal from bulk metal ingots. For example, preformed metal silicide ingots may be subjected to attrition, impact, crushing, grinding, abrasion, milling, or chemical methods to produce a particulate preformed metal silicide. Grinding is typical. The preformed metal silicide may be further classified as to particle size distribution by means of, for example, screening or by the use of mechanical aerodynamic classifiers such as a rotating classifier. Other methods of making the preformed metal silicide known in the art are also contemplated for making the preformed metal silicide of the invention. For example, the methods of making palladium silicides disclosed in U.S. Pat. No. 3,297,403 and US 2009/0275466 are contemplated. Most of the preformed metal silicides are available commercially. For example, some of the preformed metal silicides may be obtained from Alfa Aesar and ACI Alloy.

The silicon tetrahalide has the formula $SiX_4$, where X is chloro, bromo, fluoro, or iodo, alternatively chloro, bromo, or iodo, alternatively chloro.

Examples of the silicon tetrahalide include, but are not limited to, silicon tetrachloride, silicon tetrabromide, silicon tetraiodide, and silicon tetrafluoride.

Silicone tetrahalide can be made by methods known in the art. Many of these silicon tetrahalides are available commercially.

The reactor for step (i) can be any reactor suitable for treating a metal silicide with a silane gas. For example, a sealed tube, an open tube, a fixed bed, a stirred bed, and a fluidized bed reactor may be used.

The temperature at which the preformed metal silicide is treated with the hydrogen and the silicon tetrahalide is typically from 300 to 1400° C.; alternatively 400 to 1200° C., alternatively from 600 to 1200° C.; alternatively from 650 to 1100° C.

The pressure at which the preformed metal silicide is treated with the hydrogen and the silicon tetrahalide can be sub-atmospheric, atmospheric, or super-atmospheric. For example, the pressure is typically from 0 to 2000 kilopascals gauge (kPag); alternatively from 0 to 1000 kPag; alternatively from 0 to 800 kPag. As used herein, 0 kPag means atmospheric pressure.

The mole ratio of hydrogen to silicon tetrahalide in the mixture is from 0.01 to 10,000, alternatively from 1 to 100, alternatively from 2 to 20.

The hydrogen and silicon tetrahalide have a residence time sufficient for the hydrogen and silicon tetrahalide to contact the preformed metal silicide and form the treated metal silicide. For example, a sufficient residence time for the hydrogen and silicon tetrahalide is typically at least 0.01 seconds (s); alternatively at least 0.1 s; alternatively from 0.1 s to 10 min; alternatively from 0.1 s to 1 min; alternatively from 0.5 s to 10 s. As used herein, "residence time" means the time for one reactor volume of reactant gases (i.e., hydrogen and silicon tetrahalide) to pass through a reactor charged with the preformed metal silicide. The desired residence time may be achieved by adjusting the flow rate of the hydrogen and silicon tetrahalide.

When using a fluidized bed, the hydrogen and silicon tetrahalide are introduced into the reactor bed at a rate sufficient to provide a residence time as described above but also at a rate sufficient to fluidize the bed. The rate will depend upon the particle size mass distribution of the particles of preformed metal silicide in the bed and the dimensions of the fluidized bed reactor. One skilled in the art would know how to determine a sufficient rate addition to fluidize the bed while not completely elutriating the material from the bed.

The amount of preformed metal silicide in the reactor is typically at least 0.01 mg catalyst/cm³ of reactor volume; alternatively at least 0.5 mg catalyst/cm³ of reactor volume; alternatively from 1 to 10,000 mg catalyst/cm³ of reactor volume.

The order of addition of the hydrogen, the silicon tetrahalide and preformed metal silicide in step (i) is not critical. Typically, the reactor is charged with the preformed metal silicide followed by simultaneously flowing hydrogen and silicon tetrahalide through the preformed metal silicide; however, the reactor may be first charged with the hydrogen and the silicon tetrahalide followed by the preformed metal silicide. The treatment of the preformed metal silicide by by separate pulses of hydrogen and silicon tetrahalide are also envisioned.

There is no upper limit on the time for which step (i) is conducted. For example, step (i) is usually conducted for at least 0.1 seconds, alternatively from 1 second to 5 hours, alternatively from 1 minute to 1.5 hours.

Step (i) produces a treated metal silicide. The treated metal silicide typically comprises additional silicon compared to the preformed metal silicide (i.e., the untreated metal silicide). As used herein, "additional silicon" means the silicon deposited on the preformed metal silicide by treatment with the silicon tetrahalide and hydrogen in step (i). The amount of additional silicon on the treated metal silicide typically depends upon the length of time the preformed metal silicide is treated with the hydrogen and silicon tetrahalide, with longer treatment times depositing more silicon. For example, the treated metal silicide typically comprises at least 0.1 to 90% (w/w), alternatively from 1 to 20% (w/w), alternatively from 1 to 5% (w/w), based on the weight of the treated metal silicide, of additional silicon. The amount of silicon in the preformed metal silicide and the treated metal silicide may be determined using inductively coupled plasma atomic emission spectroscopy (ICP-AES) and ICP mass spectrometry (ICP-MS).

In step (ii), the treated metal silicide is reacted with an organohalide according to the formula RX at a temperature from 250 to 700° C. to form a diorganodihalosilane, wherein R is $C_1$-$C_{10}$ hydrocarbyl and X is halo.

The organohalide has the formula RX (I), wherein R is a hydrocarbyl group having 1 to 10 carbon atoms and X is halo, for example fluoro, chloro, bromo, or iodo.

The hydrocarbyl groups represented by R in formula (I) typically have from 1 to 10 carbon atoms, alternatively from 1 to 6 carbon atoms, alternatively from 1 to 4 carbon atoms. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, and decyl; cycloalkyl, such as cyclopentyl, cyclohexyl, and methylcyclohexyl; aryl, such as phenyl and naphthyl; alkaryl, such as tolyl, and xylyl; aralkyl such as benzyl and phenylethyl; alkenyl, such as vinyl, allyl, and propenyl; aralkenyl, such as styryl and cinnamyl; and alkynyl, such as ethynyl and propynyl.

Examples of organohalides include, but are not limited to, methyl chloride, methyl bromide, methyl iodide, ethyl chloride, ethyl bromide, ethyl iodide, chlorobenzene, bromobenzene, iodobenzene, vinyl chloride, vinyl bromide, vinyl iodide, allyl chloride, allyl bromide, and ally iodide.

The organohalide may be reacted by itself or mixed with an inert carrier gas in step (ii) of the method.

Methods of preparing organohalides are well known in the art; many of these compounds are commercially available.

The reactors suitable for use in (ii) are as described above for (i). The same reactor may be used for step (i) as used in step (ii); however, separate reactors may also be used.

The organohalide is typically reacted with the treated metal silicide by feeding the organohalide into a reactor containing the treated metal silicide produced in step (i).

The residence time of the organohalide is sufficient for the organohalide to react with the treated metal silicide to form a diorganodihalosilane. For example, a sufficient residence time of the organohalide is as described above for the hydrogen and silicon tetrahalide in step (i).

The quantity of the treated metal silicide in the reactor in step (ii) is as described above for the preformed metal silicide in step (i).

The temperature at which organohalide is reacted with the treated metal silicide is typically from 250 to 700° C.; alternatively from 280 to 700° C.; alternatively from 300 to 700° C.

Step (ii) is typically conducted until the silicon in the treated metal silicide falls below predetermined limits. For example, step (ii) is typically conducted until the silicon in the treated metal silicide is below 90% (w/w), alternatively from 1 to 90% (w/w), alternatively from 1 to 40% (w/w), of its initial amount in the treated metal silicide. The amount of silicon in the treated metal silicide may be determined using inductively coupled plasma atomic emission spectroscopy (ICP-AES) and ICP mass spectrometry (ICP-MS).

The pressure at which the organohalide is reacted with the treated metal silicide in (ii) can be sub-atmospheric, atmospheric, or super-atmospheric. For example, the pressure is typically from 0 to 2000 kilopascals gauge (kPag); alternatively from 0 to 1000 kPag; alternatively from 0 to 800 kPag.

Step (i) and step (ii) of the method are conducted separately and consecutively. As used herein, "separately" means that the step (i) and step (ii) do not take place simultaneously. As used herein, "consecutively" means that step (ii) is performed after step (i) in the method; however, additional steps may be after step (i) and before step (ii), such as described below.

In one embodiment, the method further comprises (iii) contacting the treated metal silicide reacted with the organohalide in (ii) with the mixture comprising hydrogen gas and a silicon tetrahalide to reform the treated metal silicide; and (iv) contacting the reformed treated metal silicide with the organohalide to form at least one diorganodihalosilane. Step (iii) is conducted as described for step (i), and step (iv) is conducted as described for step (iv) above.

In another embodiment, the method of the invention further comprises repeating steps (iii) and (iv) at least 1 time, alternatively from 1 to $10^5$ times, alternatively from 1 to 1000 times, alternatively from 1 to 100 times, alternatively from 1 to 10 times.

The method may further comprise pre-heating and gasifying the organohalide or silicon tetrahalide by known methods prior to treating the preformed metal silicide with the silicon tetrahalide and hydrogen in (i) and (iii) or reacting the organohalide with the treated metal silicide in (ii) and (iv). Alternatively, the method may further comprise bubbling the hydrogen through liquid silicon tetrahalide to vaporize the silicon tetrahalide prior to contacting with the preformed metal silicide in step (i) and the treated metal silicide in (iii).

The method may further comprise activating the preformed metal silicide prior to treating with the silicon tetrahalide and hydrogen in (i) and (iii) or activating the treated metal silicide prior to reacting the organohalide with the treated metal silicide in (ii) and (iv). As used herein, "activating" means to contact the preformed metal silicide or the treated metal silicide with hydrogen at elevated temperature, typically around 500° C.

In one embodiment, the treated metal silicide is reacted with the organohalide in step (ii) in the absence of a least one of hydrogen gas or the silicon tetrahalide, wherein the silicon tetrahalide is as described and exemplified above.

The method may further comprise recovering the diorganodihalosilane produced. The diorganodihalosilane may be recovered by, for example, removing gaseous diorganodihalosilane from the reactor followed by isolation by distillation.

The diorganodihalosilane produced by the method described and exemplified above has the formula $R_2SiX_2$, wherein R and X are as defined and exemplified above for the organohalide.

Examples of diorganodihalosilanes prepared according to the present method include, but are not limited to, dimethyldichlorosilane (i.e., $(CH_3)_2SiCl_2$), dimethyldibromosilane, dimethyldiiodosilane, dimethyldifluorosilane, diethyldichlorosilane, diethyldibromosilane, diethyldiiodosilane, dicyclohexyldichlorosilane, and dicyclohexyldibromosilane.

The method may also produce other organohalosilanes, such as those having the formula $R_aHSiX_{3-a}$, $RSiX_3$, and $R_3SiX$, where R and X are as defined above and a is 1 or 2. The method may also produce hydrohalosilanes, such as those having the formula $HSiX_3$, where X is as defined above.

The method of the present invention produces diorganodihalosilanes from silicon tetrahalide and metal silicide. Since silicon tetrahalide is a byproduct of other industrial processes and metal silicide may may be produced using less energy than required to produce zero-valent silicon, the method of the invention may be more economical than methods of producing diorganodihalosilanes using zero-valent silicon. Further, the method allows the production of diorganodihalosilanes from metal silicides that typically do not produce diorganodihalosilanes when reacted directly with an organohalide.

The method of the present invention produces diorganodihalosilanes that can be hydrolyzed in known methods for producing polyorganosiloxanes. The polyorganosiloxanes thus produced find use in many industries and applications.

EXAMPLES

The following examples are presented to better illustrate the method of the present invention, but are not to be considered as limiting the invention, which is delineated in the appended claims. Unless otherwise noted, all parts and percentages reported in the examples are by weight. The following table describes the abbreviations used in the examples:

TABLE 2

List of abbreviations used in the examples.

| Abbreviation | Word |
| --- | --- |
| g | gram |
| mg | milligram |
| Me | methyl |
| wt. | weight |
| % | percent |
| mol | mole |
| hr or h | hours |
| min | minutes |
| s | seconds |
| ° C. | degrees Celsius |
| NA | not applicable |
| mL | milliliters |
| μL | microliters |
| cm | centimeter |
| GC-MS | gas chromatography-mass spectrometry |
| ICP-AES | inductively coupled plasma-atomic emission spectroscopy |
| Silicon Conversion | $\dfrac{(\text{wt. Si in sample before reaction} - \text{wt. Si in sample after reaction})}{(\text{wt Si in sample before reaction}) \times 100} \times 100$ |

The following methods and materials were employed in the examples:

The reaction products were analyzed by GC-MS using an Agilent Technologies 6890N Network GC system with 5975B inert XL EI/CI MSD to determine selectivity.

Concentration of silicon and other elements were determined by ICP-AES. The method was a typical procedure known for elemental analysis of solid samples, wherein the solids were dissolved in HF and the concentration in aqueous solution determined with respect to appropriate standards containing known amounts of any elements of interest.

Methyl chloride (>99.9% (w/w) purity is available from Airgas. The preformed metal silicides are available from Alfa Aesar (Ward Hill, Mass.) and ACI Alloy (San Jose, Calif.).

The flow-through, metal reactor tube set-up consisted of a 0.25 inch stainless steel tube placed either vertically or horizontally. The preformed metal silicide to be tested was positioned in the middle of the tube, and the organohalide was introduced from the top end of the vertically aligned tube and from one of the ends of the horizontally aligned tubes. The product and unreacted organohalide were removed from the end of the tube opposite the organohalide introduction and passed through a cold trap at −78° C. The organohalide is fed to the reactor from a gas cylinder via a mass controller.

Comparative Example 1

A sample of $Pd_2Si$ (200.0 mg) was loaded into a flow-through, metal reactor and pretreated with nitrogen flow at 150° C. overnight. Next, MeCl (30 mL/min) was flowed through the catalyst bed continuously at reaction temperature of 400° C. for 4 h, 450° C. for 1.5 h, and 500° C. for 2 h. The remaining solids left in the tube were analyzed by ICP-AES, and the Si conversion was determined to be 82.8% (w/w). $MeSiCl_3$ was the only organohalosilane in the product as measured by GC.

Example 1

A sample of $Pd_2Si$ (350.0 mg) was loaded into the flow-through, metal reactor and reduced with $H_2$ (24 mL/min) at 850° C. for 60.0 min. Next, a $H_2$ and $SiCl_4$ gas mixture ($H_2/SiCl_4$ molar ratio of 2.8 to 8.6) was fed into the $Pd_2Si$ bed at 850° C. for 2.0 h. During this treatment process, trace amounts of $HSiCl_3$ product were seen by GC/GC-MS analysis. The $H_2$ and $SiCl_4$ gas mixture flow was stopped and replaced with nitrogen and the reaction temperature was reduced to 400° C. The system was then purged with $N_2$ (50 mL/min) at 400° C. for 60 min. Next, MeCl (30 mL/min) was flowed through the treated $Pd_2Si$ bed at 400° C., and the products were analyzed by GC and GC-MS. The silane products detected were $SiCl_4$ (3% (w/w)), $Me_2SiCl_2$ (11% (w/w)) and $MeSiCl_3$ (86% (w/w)). After 30 min at 400° C., products detected were, approximately, $SiCl_4$ (7.7% (w/w)), $Me_2SiCl_2$ (5.7% (w/w)) and $MeSiCl_3$ (87% (w/w)).

Example 2

A sample of $Pd_2Si$ (510.0 mg) was loaded into the flow-through, metal reactor and reduced with $H_2$ (24 mL/min) at 700° C. for 120 min. Next, a $H_2$ and $SiCl_4$ gas mixture ($H_2/SiCl_4$ molar ratio from 2.8 to 10) was fed into the $Pd_2Si$ bed at 850° C. for 2 h. During this treatment process, production of $HSiCl_3$ (1.3-2% (w/w), based on the wt. of Si-containing materials exiting the reactor) was measured by GC/GC-MS. The $H_2$ and $SiCl_4$ gas flow was stopped and replaced with nitrogen, and the reaction temperature was reduced to 400° C. The system was purged with $N_2$ (50 mL/min) at 400° C. for additional 60 min. Next, MeCl (30 mL/min) was flowed through the treated $Pd_2Si$ bed at 400° C., and the products were analyzed by GC and GC-MS. The silane products from the reactor were $SiCl_4$ (2% (w/w)), $Me_2SiCl_2$ (24% (w/w)) and $MeSiCl_3$ (74% (w/w)).

Example 3

A sample of $Pd_9Si_2$ (670.0 mg) was loaded into the flow-through, metal reactor and reduced with $H_2$ (24 ml/min) at 650° C. for 120 min. Next, $H_2$ and $SiCl_4$ gas mixture ($H_2/SiCl_4$ molar ratio 10 to 15) was fed into the $Pd_9Si_2$ bed at 650° C. for 2 h. During this treatment process, generation of $HSiCl_3$ product was not seen in GC/GC-MS. The flow of hydrogen and silicon tetrachloride was stopped and replaced with nitrogen and the reaction temperature was allowed to reach to 400° C. The system was purged with $N_2$ (50 ml/min) at 400° C. for additional 60 min. Next MeCl (30 mL/min) was flowed through the treated $Pd_9Si_2$ bed at 400° C., and the products were analyzed by GC and GC-MS. Evolution of chlorosilanes as observed were $SiCl_4$ and $MeSiCl_3$. No $Me_2SiCl_2$ was detected.

Example 4

A sample of $Pd_3Si$ (650.0 mg) was loaded into the flow-through, metal reactor and reduced with $H_2$ (12 ml/min) at 650° C. for 120 min. Next, a $H_2$ and $SiCl_4$ gas mixture (H2/SiCl4 molar ratio from 10 to 12) was fed into the $Pd_3Si$ bed at 650° C. for 2 h. During this treatment process, generation of trace amounts of $HSiCl_3$ were seen in GC/GC-MS. The flow of $H_2$ and $SiCl_4$ was stopped and replaced with nitrogen, and the reaction temperature was reduced to 400° C. The system was purged with $N_2$ (50 ml/min) at 400° C. for additional 60 min. Next MeCl (6 mL/min) was flowed through the treated $Pd_3Si$ bed at 350-400° C., and the products were analyzed by GC and GC-MS. Trace amount of $Me_2SiCl_2$ (~1% (w/w)) were seen in addition to $SiCl_4$ and $MeSiCl_3$ as the major chlorosilanes products.

Example 5

A sample of $Pt_2Si$ (800.0 mg) was loaded into the flow-through, quartz tube inserted metal tube reactor and reduced with $H_2$ (30 ml/min) at 500° C. for 120 min. The temperature was increased to 850° C. and $H_2$ and $SiCl_4$ gas mixture ($H_2/SiCl_4$ molar ratio from 10 to 12) was fed into the activated $Pt_2Si$ bed at 850° C. for 0.5 h. During this treatment process, production of $HSiCl_3$ was observed in GC/GC-MS. The flow of $H_2$ and $SiCl_4$ was stopped and replaced with hydrogen, and the reaction temperature was lowered down to 300° C. Hydrogen flow was stopped at 300° C. and the system was purged with Argon for additional 60 min. Next MeCl (5 mL/min) was flowed through the treated $Pt_2Si$ bed at 350-500° C., and the products were analyzed by GC and GC-MS. Chlorosilanes product evolution observed at different reaction temperature was summarized, as follow. At T=300-400° C., only $SiCl_4$ was produced. Methyl chloride flow through at T=500° C. after 10 min showed $SiCl_4$ (15%), $Me_2SiCl_2$ (25%), $MeSiCl_3$ (60%). As the reaction continued the concentration of $Me_2SiCl_2$ decreases; after 20 min the species evolved were $SiCl_4$ (3%), $Me_2SiCl_2$ (36%), $MeSiCl_3$ (61%) and after 30 min, $SiCl_4$ (3%), $Me_2SiCl_2$ (21%), $MeSiCl_3$ (76%) were observed.

Example 6

A sample of $Ni_2Si$ (800.0 mg) was loaded into the flow-through, quartz tube inserted metal tube reactor and reduced with H$_2$ (30 ml/min) at 500° C. for 120 min. The temperature was increased to 850° C., and a mixture of H$_2$ and SiCl$_4$ gases (H$_2$/SiCl$_4$ molar ratio from 10 to 12) was fed into the activated Ni$_2$Si bed at 850° C. for 0.5 h. During this treatment process, production of HSiCl$_3$ was observed in GC/GC-MS. The flow of H$_2$ and SiCl$_4$ was stopped and replaced with hydrogen, and the reaction temperature was lowered down to 300° C. Hydrogen flow was stopped at 300° C. and the system was purged with Argon for additional 60 min. Next, MeCl (5 mL/min) was flowed through the treated Ni$_2$Si bed at 350-500° C., and the products were analyzed by GC and GC-MS. At T=350° C., chlorosilanes as observed were SiCl$_4$ (18%), Me$_2$SiCl$_2$ (5%), MeSiCl$_3$ (76%); at T=450° C., HSiCl$_3$ (4%), MeHSiCl$_2$ (3%), SiCl$_4$ (34%), MeSiCl$_3$ (63%), and at T=500° C., HSiCl$_3$ (5%), SiCl$_4$ (77%), MeSiCl$_3$ (18%).

That which is claimed is:

1. A method of preparing a diorganodihalosilane, the method comprising the following separate and consecutive steps:
   (i) treating a preformed metal silicide with a mixture comprising hydrogen gas and a silicon tetrahalide at a temperature from 300 to 1400° C. to form a treated metal silicide, wherein the preformed metal silicide comprises a metal selected from at least one of Ni, Pd, or Pt; and
   (ii) reacting the treated metal silicide with an organohalide according to the formula Rx at a temperature from 250 to 700° C. to form a diorganodihalosilane, wherein R is C$_1$-C$_{10}$ hydrocarbyl and X is halo.

2. The method of claim 1, wherein the preformed metal silicide is a palladium silicide.

3. The method of claim 2, wherein the preformed metal silicide is selected from at least one of PdSi, Pd$_2$Si, Pd$_3$Si, or Pd$_2$Si$_9$.

4. The method of claim 3, wherein the preformed metal silicide is Pd$_2$Si.

5. The method of claim 1, wherein the preformed metal silicide is Pt$_2$Si or Ni$_2$Si.

6. The method of claim 1, wherein step (i) is at a temperature from 650 to 1100° C. and step (ii) is at a temperature from 300 to 700° C.

7. The method of claim 1, wherein the diorganodihalosilane is according to the formula R$_2$SiX$_2$.

8. The method of claim 1, wherein R is methyl and X is chloro.

9. The method of claim 1, further comprising activating the preformed metal silicide prior to step (i).

10. The method of claim 1, further comprising (iii) contacting the treated metal silicide reacted with the organohalide in (ii) with the mixture comprising hydrogen gas and the silicon tetrahalide to reform the treated metal silicide, and (iv) contacting the reformed treated metal silicide with the organohalide to form the diorganodihalosilane.

11. The method of claim 1, further comprising recovering the diorganodihalosilane.

12. The method of claim 1, wherein the mole ratio of hydrogen to silicon tetrahalide in the mixture is from 2 to 20.

13. The method of claim 1, wherein the hydrogen and silicon tetrahalide have a residence time from 0.5 s to 10 s.

14. The method of claim 1, wherein the organohalide has a residence time from 0.5 s to 10 s.

15. The method of claim 1, further comprising activating the treated metal silicide after step (i) and prior to step (ii).

16. The method of claim 1, wherein the treated metal silicide is reacted with the organohalide in step (ii) in the absence of a least one of hydrogen gas or the silicon tetrahalide.

17. A method of preparing a diorganodihalosilane, the method comprising the following separate and consecutive steps:
   (i) treating a preformed metal silicide with a mixture comprising hydrogen gas and a silicon tetrahalide at a temperature from 300 to 1400° C. to form a treated metal silicide, wherein the preformed metal silicide is selected from at least one of Pt$_2$Si, Ni$_2$Si, PdSi, Pd$_2$Si, Pd$_3$Si, or Pd$_2$Si$_9$; and
   (ii) reacting the treated metal silicide with an organohalide according to the formula Rx at a temperature from 250 to 700° C. to form a diorganodihalosilane, wherein R is C$_1$-C$_{10}$ hydrocarbyl and X is halo.

18. The method of claim 1, further comprising:
   (iii) hydrolyzing the diorganodihalosilane to form a polyorganosiloxane.

* * * * *